(12) United States Patent
Velliste et al.

(10) Patent No.: US 8,818,557 B2
(45) Date of Patent: Aug. 26, 2014

(54) CORTICAL CONTROL OF A PROSTHETIC DEVICE

(75) Inventors: Meel Velliste, Pittsburgh, PA (US); Sagi Perel, Pittsburgh, PA (US); Andrew S. Whitford, Pittsburgh, PA (US); Andrew Schwartz, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 711 days.

(21) Appl. No.: 12/935,680

(22) PCT Filed: Mar. 18, 2009

(86) PCT No.: PCT/US2009/037508
§ 371 (c)(1),
(2), (4) Date: Nov. 16, 2010

(87) PCT Pub. No.: WO2009/145969
PCT Pub. Date: Dec. 3, 2009

(65) Prior Publication Data
US 2011/0060461 A1    Mar. 10, 2011

Related U.S. Application Data

(60) Provisional application No. 61/041,702, filed on Apr. 2, 2008, provisional application No. 61/052,466, filed on May 12, 2008.

(51) Int. Cl.
*A61F 2/70* (2006.01)
*G05B 19/042* (2006.01)

(52) U.S. Cl.
USPC .............. 700/254; 700/253; 623/57; 623/60

(58) Field of Classification Search
USPC ................ 700/254, 253, 245, 250; 600/544; 623/25, 57, 59, 60, 61
See application file for complete search history.

(56) References Cited

U.S. PATENT DOCUMENTS

2005/0159668 A1* 7/2005 Kemere et al. ............ 600/544
2011/0224572 A1* 9/2011 Gilja et al. ................. 600/545

FOREIGN PATENT DOCUMENTS

WO    03/041790    5/2003

OTHER PUBLICATIONS

Wolpaw, Jonathan R. et al., "Brain-computer interfaces for communication and control", Clinical Neurophysiology 113 (2002) 767-791.
Wessberg, Johan et al, "Real-time trajectory by ensembles of coritcal neurons in primates", Nature, vol. 408, Nov. 16, 2000, pp. 361-365.
Wahnoun, Remy et al., "Selection and parameterization of cortical neurons for neuroprosthetic control", J. Neural Eng. 3 (2006) 162-171.
Taylor, Dawn M. et al., "Direct cortical Control of 3D Neuroprosthetic Devices", Science 296, 1829-1832 (2002).
Schwartz, Andrew B. et al., "Brain-Controlled Interfaces: Movement Restoration with Neural Prosthetics", Neuron 52, 205-220, Oct. 5, 2006.

(Continued)

*Primary Examiner* — Ronnie Mancho
(74) *Attorney, Agent, or Firm* — Eckert Seamans Cherin & Mellott, LLC; Philip E. Levy

(57) ABSTRACT

A methodology for using cortical signals to control a multi jointed prosthetic device for direct real-time interaction with the physical environment, including improved methods for calibration and training.

42 Claims, 2 Drawing Sheets

(56) References Cited

OTHER PUBLICATIONS

Schwartz, Andrew B., "Cortical Neural Prosthetics", Annu. Rev. Neurosci., 2004.27:487-507.
Schwartz, Andrew B. et al, "Motor Cortical Activity During Drawing Movements: Population Representation During Lemniscate Tracing", Journal of Neurophysiology 82:2705-2718, 1999.
Schwartz, Andrew B. et al., "Primate Motor cortex and Free Arm Movements to Visual Targets in Three-Dimensional Space. I. Relations Between Single Cell Discharge and Direction of Movement", The Journal of Neuroscience, Aug. 1988, 8(8): 2913-2927.
Santhanam, Gopal et al, "A high-performance brain-computer interface", vol. 442, Jul. 13, 2006, doi:10.1038/nature04968.
Sanchez, Justin C. et al, "Interpreting Spatial and Temporal Neural Activity Through a Recurrent Neural Network Brain-Machine Interface", IEEE Transactions on Neural Systems and Rehabilitation Engineering, vol. 13, No. 2, Jun. 2005.
Reina, G. Anthony et al, "On the Relationship Between Joint Angular Velocity and Motor Cortical Discharge During Reaching", J. Neurophysiol 85:2576-2589, 2001.
Moran, Daniel W. et al, "Motor Cortical Activity During Drawing Movements: Population Representation During Spiral Tracing", J Neurophysiol 82:2693-2704, 1999.
Moran, Daniel W. et al., "Motor cortical Representation of Speed and Direction During Reaching", J Neurophysiol 82:2676-2692, 1999.
Leuthardt, Eric C. et al, "The Emerging World of Motor Neuroprosthetics: A Neurosurgical Perspective", vol. 58, No. 7, Jul. 2006.
Lebedev, Mikhail A. et al., "Cortical Ensemble Adaptation to Represent Velocity of an Artificial Actuator Controlled by a Brain-Machine Interface", The Journal of Neuroscience, May 11, 2005, 25(19):4681-4693.
Kang, Tao et al., "Determining Natural Arm Configuration Along Reaching Trajectory", Proceedings of the 25th Annual International Conference of the IEEE EMBS, Cancun, Mexico, Sep. 17-21, 2003.
Brockwell, A.E. et al., "Recursive Bayesian Decoding of Motor Cortical Signals by Particle Filtering", J Neurophysiol 91:1899-1907, 2004.
Yu, Byron M. et al., "Mixture of Trajectory Models for Neural Decoding of Goal-Directed Movements", J Neurophysiol 97:3763-3780, Jan. 28, 2007.
Graziano, Michael S. A. et al., "The cortical Control of Movement Revisited", Neuron, vol. 36, Issue 3, Oct. 24, 2002, pp. 349-362; http://www.sciencedirect.com/science?_ob=ArticleURL&_udi=B6WSS . . .
Georgopoulos, Apostolos P. et al., "Primate Motor Cortex and Free Arm Movements to Visual Targets in Three-Dimensional Space. II. Coding of the Direction of Movement by a Neuronal Population", The Journal of Neuroscience, Aug. 1988, 9(8): 2928-2937.
Kennedy, P.R., "Direct Control of a Computer from the Human Central Nervous System", IEE Transactions on Rehabilitation Engineering, vol. 8, No. 2, Jun. 2000.
Tillery, S.I. Helms et al., "The general utility of a neuroprosthetic Device under direct cortical control", Proceedings of the 25th Annual International Conference of the IEEE EMBS, Cancun, Mexico, Sep. 17-21, 2003, pp. 2043-2046.
Morasso, P., "Spatial Control of Arm Movements", Experimental Brain Research (1981) 42: 223-227.
Schwartz, Andrew B., "Direct cortical Representation of Drawing", Science, New Series, vol. 265, No. 5171 (Jul. 22, 1994), pp. 540-542.
Taylor, Dawn M. et al, "Direct cortical Control of 3D Neuroprosthetic Devices", www.sciencemag.org, Science, vol. 296, Jun. 7, 2002, pp. 1829-1832.

Musallam, S. et al, "Cognitive Control Signals for Neural Prosthetics", www.sciencemag.org, Science, vol. 305, Jul. 9, 2004, pp. 258-262.
Wolpaw, Jonathan R. et al., "Control of a two-dimensional movement signal by a noninvasive brain-computer interface in humans", PNAS, Dec. 21, 2004, vol. 101, No. 51, pp. 17849-17854.
Chapin, John K. et al., "Real-time control of a robot arm using simultaneously recorded neurons in the motor cortex", nature neuroscience, vol. 2, No. 7, Jul. 1999, pp. 664-670.
Kang, Tao et al., "Determining Natural Arm Configuration Along Reaching Trajectory", Proceedings of the 25th Annual International Conference of the IEEE EMBS, Cancun, Mexico, Sep. 17-21, 2003. pp. 1444-1447.
Lotze, Martin et al, "Phantom movements and pain an fMRI study in upper limb amputees", Brain (2001), 124, 2268-2277.
Kennedy, Philip R. et al, "computer Control Using Human Intracortical Local Field Potentials", IEEE Transactions on Neural Systems and Rehahbilitation Engineering, vol. 12, No. 3, Sep. 2004, pp. 339-344.
Leuthardt, Eric C. et al., "A brain-computer interface using electrocorticographic signals in humans", Journal of Neural Engineering, 1 (2004) 63-71.
Wahnoun, R. et al., "Neuron Selection and visual training for population vector based cortical control", Proceedings of the 26th Annual International Conference of the IEEE EMBS, San Francisco, California, Sep. 1-4, 2004, pp. 4607-4610.
Kennedy, P.R. et al., "Restoration of neural output from a paralyzed patient by a direct brain connection", NeuroReport 9, 1707-1711 (1998).
Taylor, Dawn M. et al., "Information Conveyed Through Brain-Control: Cursor Versus Robot", IEEE Transactions on Neural Systems and Rehabilitation Engineering, vol. 11, No. 2, Jun. 2003, pp. 195-199.
Gage, Gregory J. et al., "Naive coadaptive cortical control", J. Neural Eng. 2 (2005) 52-63.
Serruya, M.D. et al., "The Braingate Pilot Trial: Building and Testing a Novel Direct Neural Output for Patients with Severe Motor Impairment", http://sfn.scholarone.com/itin2004/main.html?new_page_id=126&abstract_id=4083&p_nu . . . , Feb. 2, 2007.
Kang, Tao et al., "Angle of Elbow Elevation Depends on the Reach Target Coordinates", Proceedings of the Second Joint EMBS/BMES Conference, Houston, TX, USA, Oct. 23-26, 2002, pp. 2571-2572.
Kipke, Daryl R. et al, "Silicon-Substrate Intracortical Microelectrode Arrays for Long-Term Recording of Neuronal Spike Activity in Cerebral Cortex", IEEE Transactions on Neural Systems and Rehabilitation Engineering, vol. 11, No. 2, Jun. 2003, pp. 151-155.
Serruya, Mijail D. et al, "Instant Neural Control of a Movement Signal", Nature, vol. 416, Mar. 14, 2002, pp. 141-142.
Hochberg, Leigh R. et al., "Neuronal ensemble control of prosthetic devices by a human with tetraplegia", Nature, vol. 442, Jul. 2006, doi:10.1038/nature04970, pp. 164-171.
Helms, S.I, et al., "Training in Cortical Control of Neuroprosthetic Devices Improves Signal Extraction from Small Neuronal Ensembles", Reviews in the Neurosciences, 14, 107-119 (2003).
Schwartz, Andrew B., "Cortical neural Prosthetics", Annu. Rev. Neurosci. 2004 27:487-507.
Taylor, Dawn M. et al., "Direct Cortical Control of 3D Neuroprosthetic Devices", Science, vol. 296, Jun. 7, 2002, pp. 1829-1832.
J.F. Soechting, "Effect of Target Size on Spatial and Temporal Characteristcs of a Pointing Movement in Man", Experimental Brain Research, 1984, vol. 54, pp. 121-132.

* cited by examiner

CORTICAL CONTROL OF A PROSTHETIC DEVICE

CROSS-REFERENCE TO RELATED APPLICATIONS

This application is the U.S. National Stage of PCT/US2009/037508 which claims the benefit of U.S. Provisional Application No. 61/041,702, entitled "Cortical Control of a Prosthetic Arm for Self-Feeding," Which was filed on Apr. 2, 2008, and U.S. Provisional Application No. 61/052,466, entitled "Cortical Control of a Prosthetic Device," which was filed on May 12, 2008, the disclosures of which are incorporated herein by reference.

GOVERNMENT INTERESTS

This work was supported in part by the National Institute of Health under Contracts NIH NO1-NS-2-2346 and NIH R01-NS050256-01A2-04 and by DARPA under Contract W911NF-06-1-0053. The Government may have certain rights in this invention.

FIELD OF THE INVENTION

The present invention relates to prosthetic devices, and in particular to the direct cortical control of prosthetic devices based on cortical signals measured by electrodes implanted within the brain of the subject.

BACKGROUND OF THE INVENTION

Over the last few decades, there have been a number of key developments in the study of neural control of arm movement, including the introduction of the concepts of endpoint direction representation, cosine tuning, population coding, continuous trajectory representation, and the finding that neural activity in movement-related areas of the brain such as the motor cortex can be present in the absence of actual movement in paralyzed patients. In addition, basic research over the last 25 years has shown that arm movement is well represented in populations of neurons recorded from the motor cortex. These developments, combined with advances in engineering and technology, have made it possible to create prosthetic devices that are controlled directly by cortical activity. A cortically controlled prosthetic arm would be able to restore the ability of a tetraplegic, a quadriplegic or an amputee to interact with the physical environment to, for example, perform everyday tasks such as feeding oneself, opening doors, or handing a toy to a child. Previous work has demonstrated that monkeys can use spiking activity from the motor cortex to perform closed-loop control of a cursor in 3-dimensional (3D) virtual reality (VR), and can control a robotic arm with indirect visual feedback through a 3D VR display. Others have developed systems for 1- or 2-dimensional (1D/2D) closed-loop brain-control of a cursor using spiking activity, local field potentials, or electroencephalogram activity. These developments, however, have only involved control of a cursor. Furthermore, in prior experiments where a robotic arm or hand was included in the control loop, the subjects did not use it to interact with physical objects, but instead the interaction was VR based. Because physical interaction cannot be fully simulated, the performance of a prosthetic arm cannot be fully evaluated in virtual experiments.

As will be understood, a successful movement prosthetic would have to provide direct interaction with the physical world. However, due to the physical interaction between the subject, the prosthetic device and objects in the workspace, this type of task presents a higher level of difficulty than previous virtual (cursor-control) experiments. A suitable system for use of cortical signals to control a multi jointed prosthetic device for direct real-time interaction with the physical environment has not been demonstrated in the prior art, and there is thus a need for such a system.

SUMMARY OF THE INVENTION

In one embodiment, the invention provides a method of controlling a robotic prosthetic device having a selectively openable and closable gripping element. The method includes measuring a set of one or more activity parameters, such as one or more firing rates or one or more power levels in a field potential, of each of a plurality of units of a subject, each unit being associated with one or more neurons of the subject, employing a real-time extraction algorithm to generate a four-dimensional velocity vector based on each measured set of one or more activity parameters and one or more tuning parameters, the one or more tuning parameters describing how the set of one or more activity parameters are modulated with velocity, the four-dimensional velocity vector having an x direction component, a y direction component, a z direction component, and a gripping velocity component, integrating the four-dimensional velocity vector to obtain an endpoint position and a gripping element state, and using the endpoint position and the gripping element state to generate commands for controlling movement of the prosthetic device and opening and closing of the gripping element. The real-time extraction algorithm is preferably a population vector algorithm, and the one or more tuning parameters preferably comprise, for each unit, a baseline firing rate, a preferred direction vector and a modulation depth. Preferably, the opening and closing of the gripping element is controlled in a continuous manner, so that more than just binary (open or closed) states are controlled. For emcple, the gripping lement may be moved from the open condition to a part-way closed condition and then back to an open condition in a continuous manner.

In another embodiment, the invention provides a method of generating one or more tuning parameters for use in an algorithm that generates positional information used to generate movement commands for controlling a robotic prosthetic device based on set of one or more activity parameters, such as one or more firing rates or one or more power levels in a field potential, of a plurality of units of a subject, wherein each unit is associated with one or more neurons of the subject. The tuning parameters describe how the set of one or more activity parameters are modulated with velocity. The method includes steps of automatically moving the prosthetic device to one or more locations, measuring a first set of one or more activity parameters, such as a first firing rate, of each of the units during the automatic movement step, and generating a first set of the one or more tuning parameters based on at least the first sets of one or more activity parameters, such as the first firing rates. The method further includes performing a first subject controlled movement iteration wherein: (i) the prosthetic device is moved to the one or more locations by a combination of first automatic control of the prosthetic device and first subject control of the prosthetic device, wherein the first subject control of the prosthetic device is based on a set of movement commands generated from positional information generated by the algorithm based on the first set of the one or more tuning parameters and a second set of one or more activity parameters, such as a second firing rate, of each of the units measured during the first subject controlled movement iteration, and (ii) a subsequent set of the one or more tuning parameters is generated based on at least the second set of one or more activity parameters, such as the second firing rates.

The method may further include performing one or more subsequent subject controlled movement iterations, wherein in each of the subsequent subject controlled movement iterations: (i) the prosthetic device is moved to the one or more locations by a combination of subsequent automatic control of the prosthetic device and subsequent subject control of the prosthetic device, wherein the subsequent subject control of the prosthetic device is based on the subsequent set of tuning parameters generated immediately prior to the subsequent subject controlled movement iteration in question and a subsequent set of one or more activity parameters, such as subsequent firing rate, of each of the units measured during the subsequent subject controlled movement iteration in question; and (ii) a new subsequent set of the one or more tuning parameters is generated based on at least the subsequent sets of one or more activity parameters, such as the subsequent firing rates.

Preferably, the one or more subsequent subject controlled movement iterations comprises a plurality of subsequent subject controlled movement iterations, wherein a proportion of the subsequent automatic control as compared to the subsequent subject control in each of the subsequent subject controlled movement iterations decreases with each successive one of the subsequent subject controlled movement iterations. Also preferably, in a last one of the subsequent subject controlled movement iterations, the amount of the subsequent automatic control is zero. In addition, the one or more tuning parameters for use in the algorithm preferably comprise the new subsequent set of the one or more tuning parameters generated during a last one of the subsequent subject controlled movement iterations that is performed.

The invention also provides another embodiment of a method of generating one or more tuning parameters for use in an algorithm that generates positional information used to generate movement commands for controlling a robotic prosthetic device based on firing rates of a plurality of units of a subject, wherein each unit is associated with one or more neurons of the subject, and wherein the one or more tuning parameters describe how the firing rates are modulated with velocity. The method in this embodiment includes for each of a number of trials, collecting: (i) an average firing rate of each of the units during each of a number of movement segments of the prosthetic device, and (ii) a plurality of target movement vectors during the number of movement segments of the prosthetic device, wherein each of the target movement vectors represents a normalized displacement of the prosthetic device from an initial state to a target state during the associated movement segment. The method further includes generating the one or more tuning parameters based on the average firing rates collected in each of the number of trials and the target movement vectors collected in each of the number of trials.

The generating may comprise estimating a plurality of coefficients using the average firing rates and the target movement vectors and obtaining the one or more tuning parameters from the plurality of coefficients, wherein the plurality of coefficients comprise for each unit a baseline firing rate and a vector in the preferred direction of the unit, the vector having a modulation depth as its magnitude. Furthermore, the estimating may comprise estimating the plurality of coefficients by inputting the average firing rates and the target movement vectors into a multiple linear least-squares regression.

Preferably, the one or more tuning parameters comprise, for each unit, a baseline firing rate, a preferred direction vector and a modulation depth. According to a further embodiment, the invention provides a method of training a subject to use a system including a robotic prosthetic device wherein the system employs an algorithm that generates positional information used to generate movement commands for controlling the prosthetic device based on activity parameters, such as firing rates, of a plurality of units of the subject, each unit being associated with one or more neurons of the subject. The method includes moving the prosthetic device over a period of time to a plurality of target locations based on a combination of automatic control of the prosthetic device and subject control of the prosthetic device, wherein the subject control is based on a plurality of movement commands generated by the algorithm based on measured activity parameters, such as firing rates, of the units and one or more tuning parameters describing how the activity parameters are modulated with velocity, and decreasing a proportion of the automatic control as compared to the subject control over the period of time. The automatic control may include applying a deviation gain to a movement component of the subject control. In addition, movement perpendicular to a target direction may be weighted by a deviation gain between 0 and 1, the target direction being an instantaneous direction from a current endpoint position of the prosthetic device to a current target position of the prosthetic device. The automatic control may further include applying attraction assistance based on a vector toward a target position of the prosthetic device. In one specific embodiment, the application of the deviation gain results in a deviation gain movement component, and the automatic control further comprises applying attraction assistance to the deviation gain movement component by mixing the deviation gain movement component with a vector toward a target position of the prosthetic device.

The prosthetic device may include a selectively openable and closable gripping element. In this embodiment, the algorithm may further generate information used to generate commands for opening and closing the gripping element based on the activity parameters, such as firing rates, wherein the subject control includes a movement component and a gripping component, and wherein the automatic control comprises separately modifying the movement component and the gripping component. The modifying of the gripping component is preferably based on a desired action for the gripping element.

In another embodiment, the invention provides a method of using a system including a robotic prosthetic device, wherein the system employs an algorithm that generates positional information used to generate movement commands for controlling the prosthetic device based on activity parameters of a plurality of units of the subject. The method includes calibrating the robotic prosthetic device by generating one or more tuning parameters for use in the algorithm (the one or more tuning parameters describe how the activity parameters are modulated with velocity), wherein the calibrating includes allowing the user to move the prosthetic device to a plurality of target locations in a physical interaction environment. The method further includes training the user to use the prosthetic device by allowing the user to control movement of the prosthetic device in the physical interaction environment using the algorithm. Finally, following the calibrating and training steps, the method includes allowing the user to freely control movement of the prosthetic device in the physical interaction environment using the algorithm.

In still another embodiment, the invention provides a method of enabling a subject to control a robotic prosthetic device having a plurality of functional portions, each functional portion being associated with a corresponding degree of freedom of movement of the robotic prosthetic device. The method includes measuring a set of one or more activity parameters of each of a plurality of units of a subject, each unit being associated with one or more neurons of the subject, and predicting the subject's intended movement of the prosthetic device by employing a real-time extraction algorithm to generate a normalized movement vector based on at least each measured set of one or more activity parameters, wherein the normalized movement vector has a plurality of dimensions, each dimension having one or more movement components and being associated with the degree of freedom of a corresponding one of the functional portions. The method further includes, for each of the dimensions of the normalized movement vector, scaling the one or more movement components thereof using a scaling factor to convert each of the one or more movement components of the dimension into a corresponding scaled movement component having units appropriate for describing the movement of the one of the functional portions with which the dimension is associated, wherein the units of at least one of the dimensions are different than the units of at least another of the dimensions, and generating commands for controlling movement of the prosthetic device based on each scaled movement component of each of the dimensions.

Therefore, it should now be apparent that the invention substantially achieves all the above aspects and advantages. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

BRIEF DESCRIPTION OF THE DRAWINGS

The accompanying drawings illustrate presently preferred embodiments of the invention, and together with the general description given above and the detailed description given below, serve to explain the principles of the invention. As shown throughout the drawings, like reference numerals designate like or corresponding parts.

DESCRIPTION OF THE PREFERRED EMBODIMENTS

The present invention provides a methodology for using cortical signals to control a multi jointed prosthetic device for direct real-time interaction with the physical environment, including improved methods for calibration and training. As described in greater detail elsewhere herein, in order to develop and demonstrate the methodology of the present invention, two monkeys (monkey A and monkey P) were implanted with intracortical microelectrode arrays in their primary motor cortices. Each monkey used the signals to control a robotic arm to feed itself. In particular, to demonstrate fully embodied control, the monkeys, using the set-up shown in FIG. 1 and described in more detail elsewhere herein, learned a task involving real-time physical interaction between a robotic prosthetic arm having a gripper, a food target, a presentation device (designed to record the target's 3D location) and their mouth. Each monkey had its arms restrained and the prosthetic arm was positioned next to its shoulder (See FIG. 1). As discussed in more detail elsewhere herein, neuron spiking activity was used to control the 3-dimensional (3D) arm velocity and the gripper aperture velocity in real time. Food targets were presented at arbitrary positions.

Figure 2:
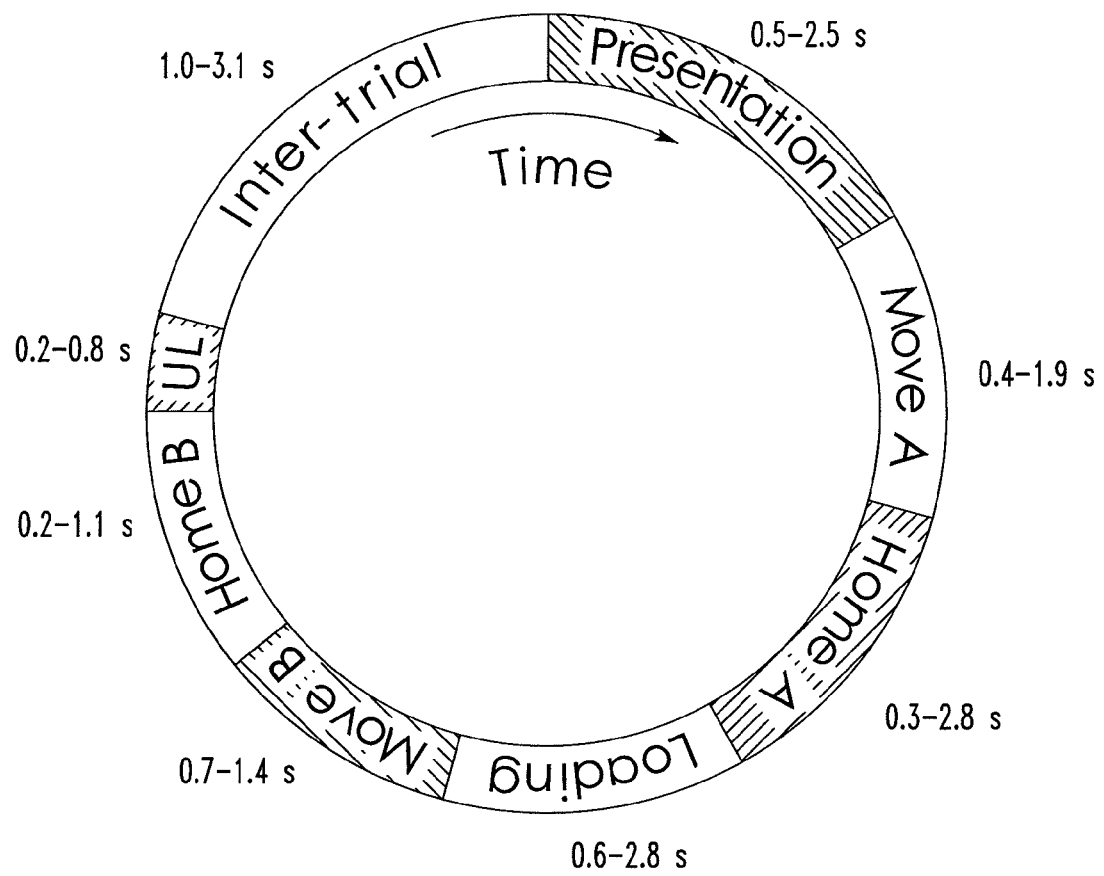
FIG. 2 is a timeline of each trial performed using the set-up of FIG. 1 divided into functional epochs.

As shown in FIG. 2, the timeline of each trial was divided into functional epochs. A trial began with a piece of food being placed on the presentation device and the device moved to a location within the monkey's workspace to provide a reaching target (Presentation). The monkey often started moving the arm forward slowly before the presentation was complete. When the target was in place, the monkey started a directed reaching movement while simultaneously opening the gripper (Move A). Upon approach, the animal made small homing adjustments to get the endpoint aligned with the target (Home A), and then closed the gripper while actively stabilizing the endpoint position (Loading). If loading was successful, the monkey made a retrieval movement back toward the mouth while keeping the gripper closed (Move B), then made small adjustments to home in on the mouth (Home B) and stabilized the endpoint while using its mouth to unload the food from the gripper (Unloading). A trial was considered successful if the monkey managed to retrieve and eat the presented food. Each trial was followed by an inter-trial period while a new piece of food was prepared for presentation (Inter-trial). During continuous self-feeding, these task epochs had no meaning during the execution of the task, but rather were imposed afterwards for purposes of data analysis. In contrast, during training and calibration, described in more detail elsewhere herein, a real-time software module kept track of the task epochs based on button-presses by a human operator and based on distance of arm endpoint from the food target presentation device tip. During training, this real-time delineation of task epochs was used so that automated assistance, also described in more detail elsewhere herein, could be applied differently during each task epoch depending on what aspect of the task the monkey was having difficulty with. During calibration, the delineation of task epochs was used so that firing rates collected during each task epoch could be regressed against appropriate behavioral correlates.

Unlike short control windows used in previous studies, each monkey controlled the arm and gripper continuously during an entire session (not only during reaching and retrieval movements but also during loading/unloading and between trials). The task was challenging due to the positional accuracy required (about 5-10 mm from the target centre position at the time of gripper closing). The required accuracy for retrieval was much lower because the monkey could move its head to meet the gripper.

The robotic arms that were used had five degrees of freedom (DOF): three at the shoulder, one at the elbow and one at the hand. Like a human arm, they permitted shoulder flexion/extension, shoulder abduction/adduction, internal/external rotation of the shoulder and flexion/extension of the elbow. The hand consisted of a motorized gripper with the movement of its two "fingers" linked, providing proportional control of the distance between them. Monkeys were first trained to operate the arm using a joystick. Their own arms were then restrained and the prosthetic arm was controlled with populations of single- and multi-unit spiking activity from the motor cortex. The neural activity was differentially modulated when food was presented at different target locations in front of the monkey. This modulation was used to represent velocity of the prosthetic arm's endpoint (a point between the fingertips of the hand/gripper) as an expression of the intention to move. The recorded signal was also used by the subject to open and close the gripper as it grasped and moved the food to the mouth. The endpoint velocity and gripper command were extracted from the instantaneous firing rates of simultaneously recorded units using a real-time extraction algorithm.

Many real-time extraction algorithms of varying complexity have been developed in open-loop or closed-loop experiments. A real-time extraction algorithm (the population vector algorithm) that functioned well in this paradigm is described in detail elsewhere herein. The population vector algorithm (PVA) that was used is similar to algorithms used in some cursor-control experiments. It relies on the directional tuning of each unit (as used herein, the term unit shall refer to a group of one or more neurons of the subject), characterized by a single preferred direction (PD) in which the unit fires maximally. The real-time population vector (PV) is essentially a vector sum of the preferred directions of the units in the recorded population, weighted by the instantaneous firing rates of the units, and was taken here to represent four dimensions—velocity of the endpoint in an arbitrary extrinsic three-dimensional Cartesian coordinate frame and aperture velocity between gripper fingers (fourth dimension). The endpoint velocity was integrated to obtain endpoint position, and converted to a joint-angular command position, for each of the robotic arm's four DOF, using inverse kinematics. DOF redundancy was solved by constraining elbow elevation in a way that resulted in natural-looking movements. The monkey's cortical command signal was decoded in small time-increments (30 ms), and as a result the control was effectively continuous and the animal was able to continuously change the speed and direction of arm movement and gripper aperture. Details of the control algorithm are provided elsewhere herein.

When the extraction algorithm was extended to include gripper control according to an embodiment of the present invention, a decision was made to treat gripper aperture velocity as a fourth dimension in the model driven by all units in the population. An alternative would have been to build a separate one-dimensional model driven by a subset of units. The choice to include gripper as a fourth dimension in a single model was predicated on the hypothesis that units would exhibit both endpoint-tuning and gripper-tuning in different relative amounts per unit. This hypothesis was found to be true and, as a result, gripper control was independent of endpoint control.

After the monkeys learned to operate the device with a joystick, as an intermediate step toward continuous self-feeding, they performed an assisted brain-controlled task where the monkey's control was mixed with automated control. The types and amounts of assistance were configurable per task epoch. For example, during the Home A and Loading periods, the training program partially guided the endpoint toward the target by adding a vector pointing toward the target to the endpoint velocity. Gripper opening was partially aided during Move A and Home A by adding a positive value to aperture velocity and closing was aided during Loading by adding a negative value. Monkey P also used another type of assistance where the amount of deviation from a straight line toward the target was limited by a gain factor. The relative proportion of all types of automated assistance in the overall control signal was reduced over several weeks until both the arm endpoint movement and gripper were controlled purely by the monkey's cortical command. Full details of the preferred assisted control paradigm are provided hereinbelow.

Furthermore, the preferred extraction algorithm is dependent on accurate estimates of the recorded units' tuning properties. At the beginning of each day, the tuning properties were estimated in a calibration procedure that did not require the monkey to move its arm. Because motor cortical units modulate their firing rates when the subject watches automatic task performance, an assisted task paradigm, described in more detail elsewhere herein, was used for calibration (as described above and below, the same paradigm was used during training). During the first iteration of four trials (one successful trial per target location), the monkey watched the automated performance of reach, grip and retrieval and then received the food. A trial was cancelled if the monkey did not appear to pay attention. Modulation evident during the first iteration was used get an initial estimate of each unit's tuning properties. During the next iteration, these initial estimates were used by the extraction algorithm to generate a signal that was mixed with the automated control. Tuning parameters were re-estimated at the end of each iteration while gradually decreasing the automated contribution until both arm movement and the gripper were fully controlled by the monkey's cortical activity.

Figure 1:
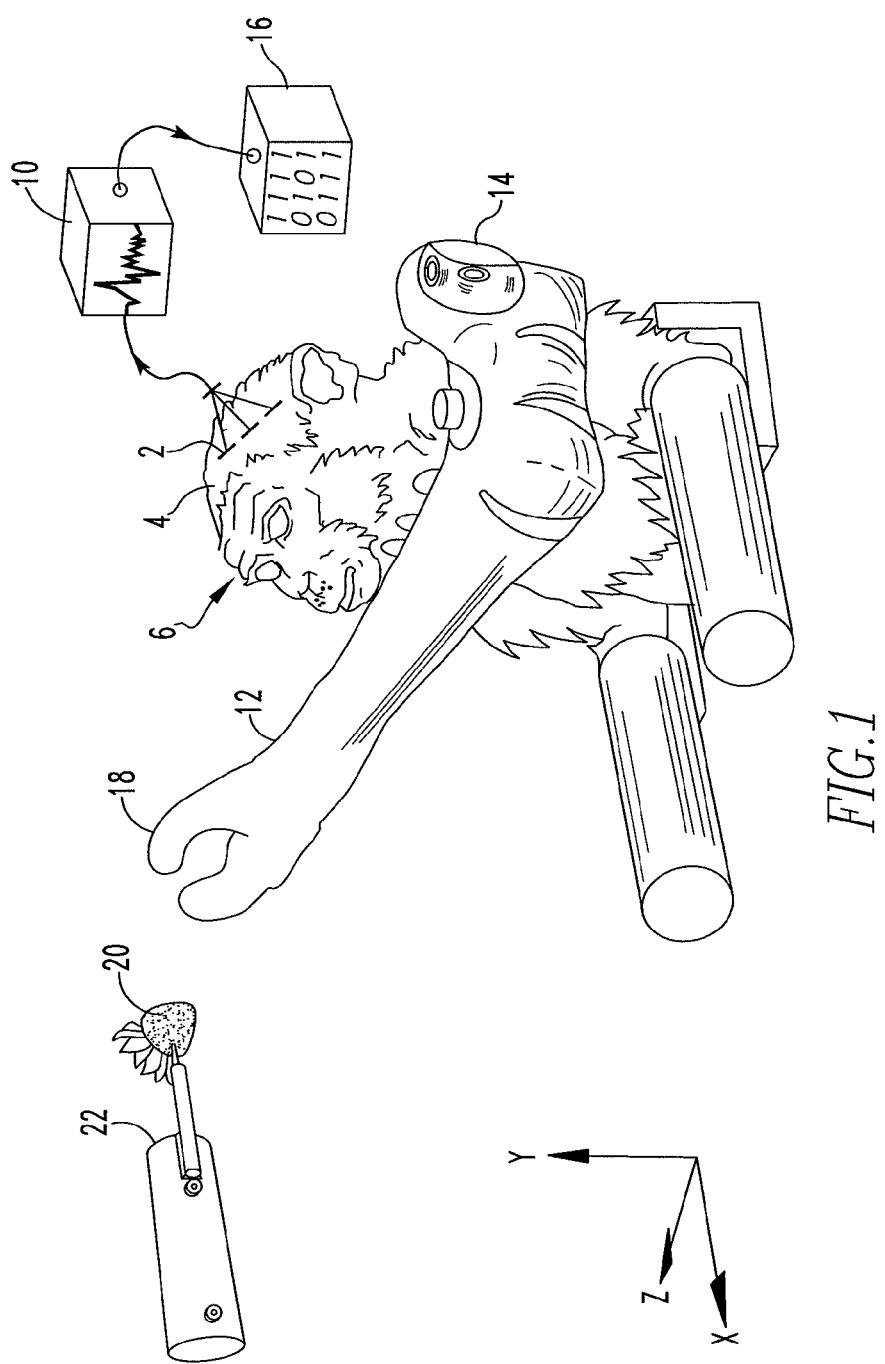
FIG. 1 is a schematic diagram of the set-up that was used during development of the methodology described herein.

FIG. 1 is a schematic diagram of the actual set-up that was used in the experimentation and development just described. Intracortical microelectrodes 2 were implanted in the proximal arm region of the primary motor cortex 4 of each monkey 6. Spike signals from units were acquired through the microelectrodes 2 using a 96-channel Plexon MAP system 10 (Plexon Inc., Dallas, Tex., USA). Monkey P had 4 microwire arrays in each hemisphere. The arrays consisted of 16 teflon-coated tungsten wires, each with a diameter of 50 µm, arranged in a 2×8 grid with 300 µm spacing. All 64 channels from the right hemisphere and 32 of the 64 from the left were connected for recording at any one time. Monkey A was implanted with a Utah array (Cyberkinetics, Inc., Foxborough, Mass., U.S.A.) in the right hemisphere, consisting of a 10×10 grid of electrodes with 400 µm spacing and a shank length of 1.5 mm. Out of the 100 electrodes on the Utah array, 96 were wired for recording and the remaining 4 were unconnected. The number of units typically isolated each day was 20-50 for monkey P (mostly from the right hemisphere, the left hemisphere typically yielded only a few or no channels with spiking activity that could be isolated). Of the 20-50 isolated units for monkey P, 10-30 were typically used for control. For monkey A, 150-180 units were isolated from the right hemisphere with 60-120 used for control. Spikes were sorted using the box-sorting and PCA methods in Plexon's SortClient software (a part of their Rasputin package). Most of the sorted units were multi-unit clusters and some were single units.

Two different prosthetic arms 12 were used over the course of the experiments. Monkey P used a custom-made anthropomorphic arm from Keshen Prosthetics (Shanghai, China). Monkey A used a standard WAM arm with a shortened upper-arm link from Barrett Technology Inc. (Cambridge, Mass., U.S.A.). The two different prosthetic arms 12 arms were functionally equivalent for the purpose of the experiments. The general shape and degrees of freedom of both arms 12 resembled that of a human arm. Both arms 12 used DC motors embedded in the arm 12 to actuate four axes: shoulder flexion, shoulder abduction, shoulder rotation and elbow flexion. The motors were servo-controlled by a servo-controller 14 in joint angular position PID mode using feedback from optical encoders (a National Instruments FW-7344 controller was used for the Keshen arm, whereas the Barrett arm came with its own Linux-based controller). Command updates were sent to the controller 14 from a computer system 16 every 30 ms. These command updates were computed from the monkey's cortical activity using the preferred extraction algorithm described elsewhere herein in the form of a Cartesian endpoint position, which was converted to joint angular positions by the robot control software. At some point during the experimentation, the Keshen arm was replaced with the Barrett arm for better mechanical stability after it was learned that the gear-driven mechanism of the Keshen arm was subject to play between the gears, resulting in free movement of the joints, even when the motor was not moving. This resulted in undesirable oscillatory deviations from the command position. The Barrett arm, on the other hand, is cable-driven, resulting in minimal play between the motors and the output shaft. The Barrett arm was able to follow the command position accurately. The Barrett arm's maximal speed at the endpoint was 2000 mm/s.

In addition to the four proximal joints, each arm 12 was fitted with a motorized two-fingered gripper 18 with a custom-made controller. The two fingers of the gripper 18 were mechanically linked so that a single motor moved both simultaneously, providing a single DOF of finger aperture control. Thus, the total DOF of the robotic system was 5 (4 for the arm and 1 for the gripper), but only 4 DOF were independently controlled using cortical signals (3 for the arm endpoint position and 1 for the gripper).

Since the control signal for the arms 12 was based on inherently noisy instantaneous firing rates, a smoothing filter (see eq. 2 hereinbelow) was used in the preferredextraction algorithm to produce a reasonably smooth control signal. The filter coefficients that were used were changed from time to time for each arm 12: a 5 sample filter, $h[k]=[0.2, 0.2, 0.2, 0.2, 0.2]$ was typically used for monkey A and an 11-sample filter $h[k]=[0.013, 0.039, 0.078, 0.123, 0.159, 0.173, 0.159, 0.123, 0.078, 0.039, 0.013]$ for monkey P. The 5-sample filter was originally used with monkey P, but was switched to the 11-sample filter to achieve smoother movements. The main results from monkey P (i.e. continuous self-feeding) are from sessions where the 11-sample filter was used. Monkey A initially used the 11-sample filter, but was switched to the 5-sample filter to reduce control delay. The main results from monkey A (i.e. continuous self-feeding) were from sessions where the 5-sample filter was used. For monkey A, the 5-sample filter provided sufficient smoothing because the population vector was less noisy due to the much higher number of recorded units compared to monkey P.

An important characteristic of a real-time control system is the delay between input and output, i.e. how long does it take before a change in the input signal is reflected in the output. The control delay can be sub-divided into system delay and memory delay. System delay is how long it takes to acquire a sample of the input signal, compute the output, and effect the output. Memory delay is a result of memory states in the control algorithm (i.e. the smoothing filters in the extraction module and the robot controller). System delay in the present embodiment was ~60 ms, consisting of spike counting delay (15 ms), software system delay (~15 ms, measured using pulses at input and output that were timed by hardware) and mechanical delay (~30 ms). Memory delay in the present embodiment was 90 ms, consisting of EM filtering delay (60 ms for the 5-sample filter) and WAM command filtering delay (30 ms). Therefore the total control delay in the present embodiment was ~60+90=~150 ms.

In order to get accurate measurements of the food target location in 3D space, food targets 20 were placed on the tip of a rigid device 22 that had infra-red emitting optical tracking markers on it. The markers were tracked using an Optotrak 3020 system (Northern Digital Inc, Waterloo, Ontario, Canada). The tip location was calculated from the marker locations using trigonometry.

The robot control module (RCM), a custom software module executed by the computer 16 and in charge of communicating with the robot controller 14, received a command from the extraction module (described elsewhere herein) every 30 ms. The RCM served the following functions: (1) apply automatic assistance and mix it with the cortical command as described elsewhere herein; (2) during training, allow the human operator to override gripper control using button presses on a control pad; (3) apply workspace limits (described below); and (4) calculate joint angular command for the robot controller from the endpoint command.

Workspace limits for monkey P were −1 mm (backward) to 201 mm (forward) for the x-dimension, −81 mm (lower) to 71 mm (upper) for the y-dimension, and −81 mm (left) to 71 mm (right) for the z-dimension. For monkey A, the limits were −20 mm (backward) to 210 mm (forward) for the x-dimension, −150 mm (lower) to 210 mm (upper) for the y-dimension, and −150 mm (left) to 150 mm (right) for the z-dimension.

As noted above, joint angles were calculated using an inverse kinematics algorithm. There were 3 degrees of freedom (DOF) to the Cartesian endpoint position (x, y and z) while the robot arm 12 had 4 DOF (angular position of each joint). In order to constrain the extra DOF, the concept of swivel angle was used. Swivel angle specifies how high the elbow is raised, defined as the angle between two planes: (1) the plane passing through the arm 12's endpoint, shoulder and elbow, and (2) the vertical plane passing through the endpoint and the shoulder. T. Kang, J. P. He, and S. I. Helms Tillery, "Determining natural arm configuration along a reaching trajectory," *Exp Brain Res* 167(3), 352 (2005), describes an algorithm that uses an energy minimization approach for finding a swivel angle, resulting in natural arm movements. For computational simplicity, and based on the observation that swivel angles calculated using the Kang et al. algorithm did not vary much within our limited workspace, a version of inverse kinematics with the swivel angle set to a constant 30 degrees was used, resulting in fairly natural-looking arm movements.

As a special case in a limited number of trials, for the continuous self-feeding task by monkey P, gripper control was implemented as a dependent degree of freedom controlled by the endpoint movement command signal based on a displacement threshold. The idea was to open the gripper when it moved forward to prepare it for gripping a target, and to close it whenever it was stabilized (designed on the assumption that the subject would stabilize it at the target). Whenever the total x-displacement (i.e. forward movement) within the latest 600 ms exceeded 50 mm, the gripper was opened. Whenever the path length in the x-dimension within the last 600 ms was below 20 mm, the gripper was closed. An additional closing criterion was based on backward movement, so that the gripper would close when the subject retracted the arm back toward its body without having loaded anything into the gripper. Whenever the x-displacement within the last 600 ms exceeded −20 mm, the gripper was closed. This gripper control algorithm was not used for monkey A, because monkey A used its cortical activity to control the gripper directly as an independent 4-th dimension as described in more detail elsewhere herein.

As discussed elsewhere herein, the endpoint velocity and gripper command for the arm 12 were extracted from the instantaneous firing rates of simultaneously recorded units using a real-time extraction algorithm. According to one particular embodiment of the present invention, the algorithm used to extract an arm control signal from the real-time stream of neural data was a version of the population vector algorithm (PVA). Specifically, given a population of N units (i={1,2,3,...,N}, each being either a single unit or multi-unit cluster) that fired $c_i[n]$ spikes during discrete time step n (i.e. between time $t_{n-1}$ and time $t_n$, where $\Delta t = t_n - t_{n-1} = 30$ ms), an "instantaneous" firing rate, $f_i[n]$, for each unit was calculated:

$$f_i[n] = \frac{c_i[n]}{\Delta t}. \qquad \text{(eq. 1)}$$

The firing rate was smoothed using a finite impulse response (FIR) filter, $h[k]$:

$$s_i[n] = \sum_{k=0}^{W-1} f_i[n-k]h[k], \qquad \text{(eq. 2)}$$

where W was the number of filter coefficients (actual values used for the coefficients during experimentation are described hereinabove). The smoothed firing rate, $s_i[n]$, was normalized using each unit's baseline rate, $b_i$, and modulation depth, $m_i$ (these parameters are obtained during calibration as described hereinbelow):

$$r_i[n] = \frac{s_i[n] - b_i}{m_i}. \qquad \text{(eq. 3)}$$

The population vector, $\vec{u}[n]$, was obtained as the vector sum of preferred directions, $\vec{p}_i$ (also obtained during calibration), weighted by the normalized firing rates, $r_i[n]$:

$$\vec{u}[n] = \frac{N_D}{N} \sum_{i=1}^{N} r_i[n]\vec{p}_i, \qquad \text{(eq. 4)}$$

where $N_D$ was the number of dimensions in $\vec{p}_i$ and $\vec{u}[n]$. Scaling by $1/N$, in eq. 4, kept the population vector in a normalized range and scaling by $N_D$ kept its magnitude from decreasing as $N_D$ was increased over the course of training (described below). The preferred direction vectors, $\vec{p}_i$, and the population vector, $\vec{u}[n]$, have components for each of the degrees of freedom of the prosthetic device that are being controlled. The fact that the components of $\vec{p}_i$ and $\vec{u}[n]$ are in normalized space, allows heterogenous degrees of freedom such as endpoint velocity and gripper aperture velocity (and, for example, wrist angular velocity in future applications) to be predicted together as part of a single vector. To convert each component from normalized space to a space with appropriate units, it is multiplied by a scaling factor. In the experiments described here, the vectors were four-dimensional ($N_D = 4$) and the components were $\vec{p}_i = \{p_{xi}, p_{yi}, p_{zi}, p_{gi}\}$ and $\vec{u}[n] = \{u_x[n], u_y[n], u_z[n], u_g[n]\}$. The first three components of $\vec{u}[n]$ were interpreted as endpoint velocity, $$\vec{v}_e[n] = k_{es}\vec{u}_{xyz}[n] + \vec{k}_{ed}, \qquad \text{(eq. 5)}$$

where $\vec{u}_{xyz}[n] = \{u_x[n], u_y[n], u_z[n]\}$, $k_{es}$ was a speed constant to convert the endpoint components of the population vector from a normalized range to a physical velocity (typically, 100 to 250 mm/s) and $\vec{k}_{ed}$ was a constant drift correction term (typically, the x-component was −15 to −40 mm/s, and the other components zero). For monkey A, on some days, the magnitude of $\vec{v}_e[n]$ was scaled by a piecewise polynomial non-linear speed gain function to allow faster reaching while not sacrificing stability at low speeds. The last component of $\vec{u}[n]$ was interpreted as the velocity of the gripper aperture, $$v_g[n] = k_{gs}u_g[n] + k_{gd}, \qquad \text{(eq. 6)}$$

where $k_{gs}$ was a speed constant to convert the gripper component of the population vector from a normalized range to a suitable command value (typically, 4 to 6 s$^{-1}$), and $k_{gd}$ was a constant drift correction term (typically 0.5 to 0.7 s$^{-1}$). The extracted velocities were integrated to obtain command position for endpoint, $$\vec{p}_e[n] = \vec{p}_e[n-1] + \vec{v}_e[n]\Delta t, \qquad \text{(eq. 7)}$$

and gripper aperture (a unitless quantity where 0 means fully closed and 1 means fully open), $$a_g[n] = a_g[n-1] + v_g[n]\Delta t \qquad \text{(eq. 8)}$$

$\vec{p}_e[n]$ and $a_g[n]$ were sent as commands to the robot control software (except when gripper control had not yet been implemented, $\vec{p}_e[n]$ was sent without $a_g[n]$). $\vec{p}_e[n]$ was interpreted as a vector in an arbitrary cartesian coordinate system with an origin and orientation that were fixed relative to the robot arm's base. The monkey was positioned next to the arm so that its mouth was at the coordinate system origin when the head was pointing directly forward.

The drift correction terms in equations 5 and 6 were necessary because an offset in endpoint velocity and gripper aperture velocity is caused by estimation error in baseline firing rate parameters, $b_i$. The estimation error is due to asymmetry in the task (monkey is more motivated on retrieval movements than reaching movements), deviation from the cosine tuning model that is implicitly assumed by the calibration model below (actual firing rates do not modulate equally above and below baseline rate) and, noise in firing rates.

As can be seen from the equations above, the extraction algorithm relied on the parameters $b_i$ (baseline firing rate), $m_i$ (modulation depth) and $\vec{p}_i$ (preferred direction), collectively called tuning parameters, that describe how each unit modulates its firing rate with arm velocity. These parameters had to be calibrated before prosthetic control could be performed. In this section, Greek symbols are used (as opposed to Latin ones in the previous section), to help distinguish the variables used in parameter calibration from variables used in read-time command extraction. For example, $\phi$ in parameter estimation (calibration) refers to an average firing rate over a whole movement period as defined below, but f in real-time extraction refers to an "instantaneous" firing rate. It has been shown that the firing rate, $\phi$, of a unit in the proximal arm area of the primary motor cortex during natural reaching in 3D space can be approximated by the model, $$\phi = \beta_o + \beta_x\upsilon_x + \beta_y\upsilon_y + \beta_z\upsilon_z, \qquad \text{(eq. 9)}$$

where $\vec{\upsilon} = \{\upsilon_x, \upsilon_y, \upsilon_z\}$ is arm endpoint velocity, $\beta_o$ is the baseline rate and $\vec{\beta} = \{\beta_x, \beta_y, \beta_z\}$ is a vector in the unit's preferred direction with the modulation depth as its magnitude. This equation has a form suitable for linear regression, allowing the tuning parameters to be estimated easily using data collected during natural arm movement. However, if the technology described herein is to be used for paralyzed persons or amputees, natural arm movement cannot be used. Furthermore, it has been shown that tuning parameters estimated from natural arm movement are not optimal for brain-controlled movement. In this embodiment of the present invention, a variation of eq. 9 is used. This variation works without natural arm movement and also adds a component for the gripper:

$$\phi_{ij} = \beta_{oi} + \beta_{xi}\delta_{xj} + \beta_{yi}\delta_{yj} + \beta_{zi}\delta_{zj} + \beta_{gi}\delta_{gi}, \quad \text{(eq. 10)}$$

This model had the same form as eq. 9, but the key distinction was that rather than using the velocity of the natural arm ($\vec{v}$ of eq. 9), it used a target displacement vector $\vec{\delta}_j = \{\delta_{xj}, \delta_{yj}, \delta_{zj}, \delta_{gj}\}$, that represented the normalized displacement from the prosthetic arm's initial state, $\vec{\zeta}_{oj} = \{\zeta_{oxj}, \zeta_{oyj}, \zeta_{ozj}, \zeta_{ogj}\}$, to the target state, $\vec{\zeta}_{Tj} = \{\zeta_{Txj}, \zeta_{Tyj}, \zeta_{Tzj}, \zeta_{Tgj}\}$, during the j-th segment of movement:

$$\vec{\delta}_j = \left\{\frac{\Delta_{xj}}{D}, \frac{\Delta_{yj}}{D}, \frac{\Delta_{zj}}{D}, \Delta_{gi}\right\}, \text{ where} \quad \text{(eq. 11)}$$

$$\vec{\Delta}_j = \{\Delta_{xj}, \Delta_{yj}, \Delta_{zj}, \Delta_{gi}\} = \vec{\zeta}_{Tj} - \vec{\zeta}_{oj}, \text{ and} \quad \text{(eq. 12)}$$

D is a normalization constant to rescale the magnitude of the x, y and z components so that all components would have a normalized range of roughly −1 to 1 (the gripper component was in that range without rescaling). The value of D was chosen arbitrarily as 220.3 mm (a fixed value representing the approximate distance from mouth at which targets were presented). In monkey P's experiments, $\vec{\delta}_j$ was defined as a unit vector in the same direction as $\vec{\Delta}_j$. $\phi_{ij}$ was the firing rate of unit i, averaged over the j-th segment of movement. Firing rates, $\phi_{ij}$, and target movement vectors, $\vec{\delta}_j$, collected over a number of movement segments over a number of trials (see the calibration procedure sections below), were input into multiple linear least-squares regression to estimate the b-coefficients of eq. 10 (the regression is performed independently for each unit, i). Finally, the tuning parameters used by the extraction algorithm were obtained from the b-coefficients:

$$b_i = \beta_{0i}, \quad \text{(eq. 13)}$$

$$m_i = |\vec{\beta}_i|, \text{ where } \vec{\beta}_i = \{\beta_{xi}, \beta_{yi}, \beta_{zi}, \beta_{gi}\}, \text{ and} \quad \text{(eq. 14)}$$

$$\vec{p}_i = \frac{\vec{\beta}_i}{|\vec{\beta}_i|}. \quad \text{(eq. 15)}$$

In one embodiment, to calibrate the tuning parameters, an iterative process was used, where initial estimates were based on observation-related activity. The monkey watched the arm automatically perform 4 successful trials consisting of reaching, loading and retrieval of a food piece from each of 4 locations in random order (lower-left, lower-right, upper-left and upper-right). The mean firing rate, $\phi_{ij}$, for each unit, i, and values for $\vec{\zeta}_{oj}$ and $\vec{\zeta}_{Tj}$, were collected for each segment of movement, j={1,2,3, . . . , J}, where J refers to the number of movement segments collected per iteration of the calibration procedure (there is one iteration per repetition of the task, as described in the assisted control paradigm section below).

The initial arm state, $\vec{\zeta}_{oj}$, was defined as the actual arm state at the beginning of the j-th movement segment. Target arm state, $\vec{\zeta}_{Tj}$, had a pre-defined value for each task epoch as shown in Table 1 below.

TABLE 1

| Task Epoch | $\vec{\zeta}_{Tej} =$ | $\zeta_{Tgj} =$ |
|---|---|---|
| Move A | $\vec{\tau}_j$ | 1 |
| Home A | $\vec{\tau}_j$ | 1 |
| Loading | $\vec{\tau}_j$ | 0 |
| Move B | $\vec{\mu}$ | 0 |
| Home B | $\vec{\mu}$ | 0 |
| Unloading | $\vec{\mu}$ | 0 |

In table 1, $\vec{\zeta}_{Tej} = \{\zeta_{Txj}, \zeta_{Tyj}, \zeta_{Tzj}\}$ refers to the endpoint component of $\vec{\zeta}_{Tj}$. $\zeta_{Tgi}$ is the gripper component of $\vec{\zeta}_{Tj}$. $\vec{\tau}_j$ is the actual location of the presented food target (based on optical tracking of the presentation device) at the beginning of movement segment, j. $\vec{\mu}$ is the nominal location of the monkey's mouth. A gripper value of 1 represents maximal aperture, and 0 represents a closed gripper.

There were 6 segments per trial, one per task epoch (Move A, Home A, Loading, Move B, Home B, and Unloading), i.e. J=6×4=24 for 4 trials. Tuning parameters were estimated from the collected data as described by equations 10-15. These initial parameters were then used by the extraction module (EM) (i.e., the software implementing the extraction algorithm described herein) to provide the monkey with partial control during the next iteration. During each iteration, another 4 trials worth of data were collected, with one successful movement cycle to each of the four locations (data from unsuccessful trials was not used). At the end of each iteration k, the cumulative data set, j={1,2,3, . . . , Jk}, was used to refine the tuning parameter estimates, the EM was updated with the new parameters to provide the monkey with better control, and the proportion of automated control decreased. Units with a modulation depth less than a cut-off, $m_i < M_c$, and units with their $r^2$-value (from regression) less than 0.1, were excluded from the population vector ($M_c$ was typically 4 Hz). A total of 4 iterations of the calibration procedure were typically performed at the beginning of a daily session, and the final estimated tuning parameters were used by the EM for the remainder of the day.

A different calibration procedure was used when gripper control had not yet been implemented in the extraction algorithm. This procedure (referred to as procedure B) was used for all of monkey P's experiments, and for the first phase of monkey A's experiments. The key difference was that in the other procedure (referred to as procedure A), data for estimating tuning parameters was collected during (at least partially) automated movement of the arm, but in procedure B, the movement was not automated while the data were collected. The fact that successful calibration was achieved with this procedure meant that observation of successful movement was not required for the subject to produce directionally modulated activity. In this procedure, the initial tuning parameters were set to arbitrary initial values ($\vec{p}_i$ was random, $b_i$ was set to 10 Hz, and $m_i$ to 50 Hz for all units). Data for tuning parameter estimation was collected during Move A and Move B while the arm was controlled completely by the EM's output. Because of the arbitrary initial settings of the tuning parameters, during the first iteration, the movement velocity was unrelated to the animal's intention, but directionally modulated activity was assumed to be present. Move A and Move B ended after a brief timeout (0.5-1 s), and proceeded to Home A or Home B, respectively. Arm movement during Home A, Loading, Home B and Unloading was completely automated. A trial was labelled "successful", as long as the animal appeared to be paying attention during both Move A and Move B. At the end of each iteration of the procedure, tuning parameters were estimated based on equations 10-15 (with the gripper component removed from each respective vector), and the new parameters were applied to real-time control during the next iteration. After each iteration of calibration, the monkey's control improved and the preferred directions quickly converged on their final values. Units with a modulation depth less than a cut-off, $m_i < M_c$, were excluded from the population vector ($M_c$ was typically 4 Hz). Unlike in the other calibration procedure, an $r^2$ cut-off was not used here. Each iteration consisted of 3 successful trials where each trial was a full movement cycle to one of 4 fixed target locations (the iterations in this version of the calibration procedure were not aligned with repetitions of the task, see the assisted control paradigm section). Food target presentation location, $\vec{\tau}_j$, in this version of the procedure, was defined as the nominal location (because the actual location was not known, since the presentation device had not yet been implemented).

According to an aspect of one embodiment of the present invention, during training and calibration, a paradigm of assisted control is used, whereby automated control is mixed with the subject's cortical control. During training, the purpose of this assistance is to shape the subject's behaviour by operant conditioning. By gradually decreasing automated assistance over a series of days, it is possible to keep each task epoch at an appropriate level of difficulty, so that the subject will stay motivated and improve. During calibration, the purpose of the assistance is to provide a behavioural template for the subject to produce modulated neural activity. During experimentation, to apply the correct type and amount of assistance at each task epoch, the robot control software kept track of task epochs in real time. At each 30 ms time step when the robot control module (RCM) received a command from the EM, it applied three types of assistance that were combined in configurable proportions per task state. Assistance was applied separately to $\vec{p}_e[n]$, the movement component of the monkey brain control command, and $a_g[n]$, the gripper component. Deviation gain was applied to $\vec{p}_e[n]$, resulting in $\vec{p}_{dg}[n]$ whereby movement perpendicular to the target direction was weighted by a "deviation gain" between 0 and 1. Target direction was defined as the instantaneous direction from the current endpoint position to the current target (the target was at the mouth for retrieval moves). This results in partially assisted 3D control where it was more difficult to go in the wrong direction than in the correct direction. A deviation gain of 0 would result in the endpoint being able to move only along a line between the mouth and the target whereas a deviation gain of 1 would result in full 3D control.

Attraction assistance was applied to obtain the effect of "attracting" the endpoint toward target by mixing $\vec{p}_{dg}[n]$ with a vector toward the target $\vec{\tau}[n]$ (eqs. 16-18).

$$p_{bc}[n] = \qquad \text{(eq. 16)}$$
$$p_{final}[n-1] + (p_{dg}[n] - p_{final}[n-1]) * MovementBCGain$$

$$AttractionVector[n] = \frac{(\vec{\tau}[n] - p_{bc}[n])}{|(\vec{\tau}[n] - p_{bc}[n])|} * AttractionSpeed * \Delta t \qquad \text{(eq. 17)}$$

$$p_{final}[n] = p_{bc}[n] + AttractionVector[n] * (1 - MovementBCGain) \qquad \text{(eq. 18)}$$

$\vec{p}_{final}[n]$ was used to move the robot arm 12. The values of MovementBCGain ranged from 0 (full automatic control) to 1 (full monkey control). AttractionSpeed was essentially a configurable constant, but as the monkey moved the arm 12 closer to the target, AttractionSpeed became slower, to prevent overshooting the target.

Gripper assistance consisted of 2 steps: calculating an assisted gripper command ag[n], and combining it with the extraction module's gripper command $a_g[n]$ from eq. 8.

$$ag[n]=ag[n-1]+GripperAssistVelocity*\Delta t \qquad \text{(eq. 19)}$$

$$a_{final}[n]=a_g[n]*GripperBCGain+ag[n]*(1-GripperBCGain) \qquad \text{(eq. 20)}$$

GripperAssistVelocity had a magnitude of GripperAssistSpeed and a sign determined by the desired action for the gripper (opening or closing). GripperAssistSpeed was usually constant within each session based on pre-set configuration, with a typical value of 3 s$^{-1}$. $a_{final}[n]$ was used to control the gripper.

Targets in the assisted training and calibration tasks were presented at 4 fixed positions for the 3D and 4D task, 2 fixed positions for the 2D training phase, and one fixed position for the 1D training phase. At the beginning of each trial, one of the fixed targets was chosen by the behavioural control software and displayed on a screen visible to the trainer, but not to the monkey (the screen was behind the monkey and slightly to the monkey's left). The trainer then presented the food at the approximate corresponding spatial location in the workspace. The fact, that the actual presented location did not exactly match the ideal target location did not matter because the only purpose of using the computer program to select targets was to keep a balanced distribution of presentations at the categorical locations (lower-left, lower-right, upper-left or upper-right). Trials were grouped into repetitions, so that at the beginning of each repetition, all targets were placed on a "to be attempted" list. For each trial, a target was randomly chosen from the list. If the trial was successful, the target was removed from the list. If the trial was unsuccessful, it remained on the list. At the beginning of the next trial, a new target was randomly chosen from the list. After three unsuccessful attempts at a given target, the target was removed from the list to keep the monkey motivated. When no targets remained on the "to be attempted" list, the repetition was over and a new one began. For example, during 4D or 3D control, this meant that a repetition could consist of 4 to 12 trials (4 if each target successful on first try, 12 if three attempts made at each target, or some number in between). This procedure helped to make sure that there would be one successful trial per target location per repetition, to keep the data balanced during a calibration procedure. It also ensured that if there was a particular target that the monkey consistently failed on during training, then that target would end up being presented more times than the other targets, giving the monkey more practice at that target. During monkey P's experiments, the presentation device had not yet been implemented, so the exact location of presentation was not known. However, the human presenter learned to be accurate because in the assisted task, the endpoint was automatically homed in on the ideal target location, giving the presenter feedback on the accuracy of their presentation.

Thus, the present invention provides a methodology for using cortical signals to control a multi jointed prosthetic device for direct real-time interaction with the physical environment. As discussed in detail herein, the invention provides a real time extraction algorithm that provides for control of 4 DOFs based on spiking activity of a number of units of the subject. In addition, the invention provides improved methods for calibration to determine appropriate tuning parameters for use by the extraction algorithm and training that preferably employ an assisted control paradigm.

While preferred embodiments of the invention have been described and illustrated above, it should be understood that these are exemplary of the invention and are not to be considered as limiting. Additions, deletions, substitutions, and other modifications can be made without departing from the spirit or scope of the present invention. For example, and without limitation, direct prosthetic control based on firing rates of units is described. However, it should be understood that other activity parameters (other then firing rates) may also be used, such as, without limitation, a power level in a local field potential for each unit. Accordingly, the invention is not to be considered as limited by the foregoing description but is only limited by the scope of the appended claims.

What is claimed is:

1. A method of generating one or more tuning parameters for use in an algorithm that generates positional information used to generate movement commands for controlling a robotic prosthetic device based on activity parameters of a plurality of units of a subject, each unit being associated with one or more neurons of the subject, said one or more tuning parameters describing how said activity parameters are modulated with velocity, the method comprising:
    automatically moving said prosthetic device to one or more locations;
    measuring a first set of one or more activity parameters of each of said units during said step of automatically moving;
    generating a first set of said one or more tuning parameters based on at least said first sets of one or more activity parameters;
    performing a first subject controlled movement iteration wherein: (i) said prosthetic device is moved to said one or more locations by a combination of first automatic control of said prosthetic device and first subject control of said prosthetic device, wherein said first subject control of said prosthetic device is based on a set of movement commands generated from positional information generated by said algorithm based on said first set of said one or more tuning parameters and a second set of one or more activity parameters of each of said units measured during the first subject controlled movement iteration; and (ii) a subsequent set of said one or more tuning parameters is generated based on at least said second sets of one or more activity parameters.

2. The method according to claim 1, further comprising performing one or more subsequent subject controlled movement iterations, wherein in each of the subsequent subject controlled movement iterations:
    (i) said prosthetic device is moved to said one or more locations by a combination of subsequent automatic control of said prosthetic device and subsequent subject control of said prosthetic device, wherein said subsequent subject control of said prosthetic device is based on the subsequent set of tuning parameters generated immediately prior to the subsequent subject controlled movement iteration in question and a subsequent set of one or more activity parameters of each of said units measured during the subsequent subject controlled movement iteration in question; and
    (ii) a new subsequent set of said one or more tuning parameters is generated based on at least said subsequent sets of one or more activity parameters.

3. The method according to claim 2, wherein said one or more subsequent subject controlled movement iterations comprises a plurality of subsequent subject controlled movement iterations, and wherein a proportion of the subsequent automatic control as compared to the subsequent subject control in each of said subsequent subject controlled movement iterations decreases with each successive one of said subsequent subject controlled movement iterations.

4. The method according to claim 3, wherein the proportion of the first automatic control as compared to the first subject control is greater than the proportion of the subsequent automatic control as compared to the subsequent subject control in each of said subsequent subject controlled movement iterations.

5. The method according to claim 4, wherein in a last one of said subsequent subject controlled movement iterations, an amount of the subsequent automatic control is zero.

6. The method according to claim 5, wherein the one or more tuning parameters for use in said algorithm comprise the new subsequent set of said one or more tuning parameters generated during a last one of said subsequent subject controlled movement iterations that is performed.

7. The method according to claim 3, wherein the one or more tuning parameters for use in said algorithm comprise the new subsequent set of said one or more tuning parameters generated during a last one of said subsequent subject controlled movement iterations that is performed.

8. The method according to claim 1, wherein the activity parameters comprise firing rates.

9. The method according to claim 2, wherein the activity parameters comprise firing rates.

10. The method according to claim 1, wherein the activity parameters comprise power levels in a local field potential.

11. The method according to claim 2, wherein the activity parameters comprise power levels in a local field potential.

12. A method of generating one or more tuning parameters for use in an algorithm that generates positional information used to generate movement commands for controlling a robotic prosthetic device based on firing rates of a plurality of units of a subject, each unit being associated with one or more neurons of the subject, said one or more tuning parameters describing how said firing rates are modulated with velocity, the method comprising:
    for each of a number of trials, collecting: (i) an average firing rate of each of said units during each of a number of movement segments of said prosthetic device, and (ii) a plurality of target movement vectors during said number of movement segments of said prosthetic device, wherein each of the target movement vectors represents a normalized displacement of the prosthetic device from an initial state to a target state during the associated movement segment; and generating the one or more tuning parameters based on the average firing rates collected in each of the number of trials and the target movement vectors collected in each of the number of trials.

13. The method according to claim 12, wherein said generating comprises estimating a plurality of coefficients using said average firing rates and said target movement vectors and obtaining said one or more tuning parameters from said plurality of coefficients, wherein said plurality of coefficients comprise for each unit a baseline firing rate and a vector in the preferred direction of the unit, the vector having a modulation depth as its magnitude.

14. The method according to claim 13, wherein said estimating comprises estimating said plurality of coefficients by inputting said average firing rates and said target movement vectors into a multiple linear least-squares regression.

15. The method according to claim 12, wherein said one or more tuning parameters comprise, for each said unit, a baseline firing rate, a preferred direction vector and a modulation depth.

16. A method of training a subject to use a system including a robotic prosthetic device, said system employing an algorithm that generates positional information used to generate movement commands for controlling the prosthetic device based on activity parameters of a plurality of units of the subject, each unit being associated with one or more neurons of the subject, the method comprising:
    moving said prosthetic device over a period of time to a plurality of target locations based on a combination of automatic control of said prosthetic device and subject control of said prosthetic device, wherein said subject control is based on a plurality of movement commands generated by said algorithm based on measured activity parameters of said units and one or more tuning parameters describing how said activity parameters are modulated with velocity; and
    decreasing a proportion of said automatic control as compared to said subject control over said period of time.

17. The method according to claim 16, wherein the activity parameters comprise firing rates.

18. The method according to claim 16, wherein the activity parameters comprise power levels in a local field potential.

19. The method according to claim 16, wherein said automatic control comprises applying a deviation gain to a movement component of said subject control.

20. The method according to claim 19, wherein movement perpendicular to a target direction is weighted by a deviation gain between 0 and 1, said target direction being an instantaneous direction from a current endpoint position of said prosthetic device to a current target position of said prosthetic device.

21. The method according to claim 19, wherein said applying a deviation gain results in a deviation gain movement component, wherein said automatic control further comprises applying attraction assistance to said deviation gain movement component by mixing said deviation gain movement component with a vector toward a target position of said prosthetic device.

22. The method according to claim 16, wherein said automatic control comprises applying attraction assistance based on a vector toward a target position of said prosthetic device.

23. The method according to claim 16, wherein said prosthetic device includes a gripping element moveable between an opened condition and a closed condition, wherein said algorithm further generates information used to generate commands for controlling movement of said gripping element based on said activity parameters, wherein said subject control includes a movement component and a gripping component, and wherein said automatic control comprises separately modifying said movement component and said gripping component.

24. The method according to claim 23, wherein said modifying said gripping component is based on a desired action for said gripping element.

25. The method according to claim 23, wherein the activity parameters comprise firing rates.

26. The method according to claim 23, wherein the activity parameters comprise power levels in a local field potential.

27. A method of controlling a robotic prosthetic device having a gripping element moveable between an opened condition and a closed condition, comprising:
    measuring a set of one or more activity parameters of each of a plurality of units of a subject, each said unit being associated with one or more neurons of said subject;
    employing a real-time extraction algorithm to generate a four-dimensional velocity vector based on each measured set of one or more activity parameters and one or more tuning parameters, said one or more tuning parameters describing how said set of one or more activity parameters are modulated with velocity, said four-dimensional velocity vector having an x direction component, a y direction component, a z direction component, and a gripping element velocity component;
    integrating an appropriately scaled version of each of said x direction component, said y direction component, an said z direction component to obtain an endpoint position and an appropriately scaled version of said gripping element velocity component to obtain a gripping element state; and
    using said endpoint position and said gripping element state to generate commands for controlling movement of said prosthetic device and opening and closing of said gripping element.

28. The method according to claim 27, wherein said real-time extraction algorithm is a population vector algorithm.

29. The method according to claim 27, wherein the activity parameters comprise firing rates.

30. The method according to claim 27, wherein the activity parameters comprise power levels in a local field potential.

31. The method according to claim 29, wherein said one or more tuning parameters comprise, for each said unit, a baseline firing rate, a preferred direction vector and a modulation depth.

32. A method of using a system including a robotic prosthetic device, said system employing an algorithm that generates positional information used to generate movement commands for controlling the prosthetic device based on activity parameters of a plurality of units of the subject, each unit being associated with one or more neurons of the subject, the method comprising:
    calibrating said robotic prosthetic device by generating one or more tuning parameters for use in said algorithm, said one or more tuning parameters describing how said activity parameters are modulated with velocity, said calibrating comprising allowing a user to move said prosthetic device to a plurality of target locations in a physical interaction environment;
    training said user to use said prosthetic device by allowing said user to control movement of said prosthetic device in said physical interaction environment using said algorithm; and following said calibrating and training, allowing said user to freely control movement of said prosthetic device in said physical interaction environment using said algorithm.

33. The method according to claim 32, wherein said training is based on a combination of automatic control of said prosthetic device and subject control of said prosthetic device, wherein said subject control is based on a plurality of movement commands generated by said algorithm based on measured activity parameters of said units and said one or more tuning parameters, and wherein said training further comprises decreasing a proportion of said automatic control as compared to said subject control over a period of time.

34. A method of enabling a subject to control a robotic prosthetic device having a plurality of functional portions, each functional portion being associated with a corresponding degree of freedom of movement of said robotic prosthetic device, comprising:
measuring a set of one or more activity parameters of each of a plurality of units of a subject, each said unit being associated with one or more neurons of said subject;
predicting said subject's intended movement of said prosthetic device by employing a real-time extraction algorithm to generate a normalized movement vector based on at least each measured set of one or more activity parameters, said normalized movement vector having a plurality of dimensions, each dimension having one or more movement components and being associated with the degree of freedom of a corresponding one of said functional portions;
for each of said dimensions of said normalized movement vector, scaling the one or more movement components thereof using a scaling factor to convert each of the one or more movement components of the dimension into a corresponding scaled movement component having units appropriate for describing the movement of the one of said functional portions with which the dimension is associated, wherein the units of at least one of the dimensions are different than the units of at least another of the dimensions; and
generating commands for controlling movement of said prosthetic device based on each scaled movement component of each of the dimensions.

35. The method according to claim 34, wherein the normalized movement vector is a normalized velocity vector, wherein the movement components of each dimension are velocity components, and wherein each scaled movement component is a scaled velocity component.

36. The method according to claim 35, wherein said generating comprises generating commands for controlling movement of said prosthetic device by integrating each scaled movement component of each of the dimensions.

37. The method according to claim 34, wherein said plurality of functional portions include a first functional portion for controlling an endpoint position of said robotic prosthetic device and a second functional portion comprising a gripper element.

38. The method according to claim 35, wherein the dimension associated with the first functional portion includes an x direction velocity portion, a y direction velocity portion, and a z direction velocity portion, and wherein the dimension associated with the second functional portion includes a gripping element velocity portion.

39. The method according to claim 34, wherein said real-time extraction algorithm is a population vector algorithm.

40. The method according to claim 34, wherein the activity parameters comprise firing rates.

41. The method according to claim 34, wherein the activity parameters comprise power levels in a local field potential.

42. The method according to claim 35, wherein said normalized velocity vector is also based on one or more tuning parameters, said one or more tuning parameters describing how said set of one or more activity parameters are modulated with velocity, and wherein said one or more tuning parameters comprise, for each said unit, a baseline firing rate, a preferred direction vector and a modulation depth.

* * * * *

UNITED STATES PATENT AND TRADEMARK OFFICE
CERTIFICATE OF CORRECTION

PATENT NO. : 8,818,557 B2
APPLICATION NO. : 12/935680
DATED : August 26, 2014
INVENTOR(S) : Meel Velliste et al.

It is certified that error appears in the above-identified patent and that said Letters Patent is hereby corrected as shown below:

On the title page item 57, second column, ABSTRACT, line 1, "multi" should read --multi- --.
In the specification
Column 1, line 10, "Which" should read --which--.
Column 2, line 4, "multi jointed" should read --multi-jointed--.
Column 2, line 39, "emcple" should read --example--.
Column 2, line 39, "lement" should read --element--.
Column 2, line 46, "on set" should read --on a set--.
Column 5, line 54, "multi jointed" should read --multi-jointed--.
Column 8, line 13, "used get" should read --used to get--.
Column 8, line 27, "Tex." should read --TX--.
Column 8, line 34, "Mass." should read --MA--.
Column 8, line 53, "Mass." should read --MA--.
Column 8, line 54, "arms 12 arms" should read --arms 12--.
Column 9, line 26, "preferredextraction" should read --preferred extraction--.
Column 10, line 59, "4-th" should read --4th--.
Column 11, line 5, "f₁[n]" should read --$f_1[n]$--.
Column 12, line 50, "but f" should read --but $f$--.
Column 13, line 7, " $\phi_{ij} = \beta_{0i} + \beta_{xi}\delta_{xj} + \beta_{yi}\delta_{yj} + \beta_{zi}\delta_{zj} + \beta_{gi}\delta_{gi}$. (eq. 10),," should read -- $\varphi_{ij} = \beta_{0i} + \beta_{xi}\delta_{xj} + \beta_{yi}\delta_{yj} + \beta_{zi}\delta_{zj} + \beta_{gi}\delta_{gi}$. (eq. 10) --.

Column 13, line 12, " $\vec{\delta}_j = \{\delta_{xj}, \delta_{yj}, \delta_{zj}, \delta_{gj}\}$ ," should read -- $\vec{\delta}_j = \{\delta_{xj}, \delta_{yj}, \delta_{zj}, \delta_{gj}\}$ --.

Column 13, line 15, " $\vec{\varsigma}_{0j} = \{\varsigma_{0xj}, \varsigma_{0yj}, \varsigma_{0zj}, \varsigma_{0gj}\}$ ," should read -- $\vec{\varsigma}_{0j} = \{\varsigma_{0xj}, \varsigma_{0yj}, \varsigma_{0zj}, \varsigma_{0gj}\}$ --.

Column 13, lines 15 and 16, " $\vec{\varsigma}_{Tj} = \{\varsigma_{Txj}, \varsigma_{Tyj}, \varsigma_{Tzj}, \varsigma_{Tgj}\}$ ," should read -- $\vec{\varsigma}_{Tj} = \{\varsigma_{Txj}, \varsigma_{Tyj}, \varsigma_{Tzj}, \varsigma_{Tgj}\}$ --.

Signed and Sealed this
Thirteenth Day of October, 2015

Michelle K. Lee
*Director of the United States Patent and Trademark Office*

CERTIFICATE OF CORRECTION (continued)
U.S. Pat. No. 8,818,557 B2

Column 13, line 20, " $\vec{\delta}_j = \{\frac{\Delta_{xj}}{D}, \frac{\Delta_{yj}}{D}, \frac{\Delta_{zj}}{D}, \Delta_{gj}\}$, where (eq. 11) ,"

should read -- $\vec{\delta}_j = \{\frac{\Delta_{xj}}{D}, \frac{\Delta_{yj}}{D}, \frac{\Delta_{zj}}{D}, \Delta_{gj}\}$, where (eq. 11) --.

Column 13, line 22, " $\vec{\Delta}_j = \{\Delta_{xj}, \Delta_{yj}, \Delta_{zj}, \Delta_{gj}\} = \vec{\varsigma}_{Tj} - \vec{\varsigma}_{0j}$, and (eq. 12) ,"

should read -- $\vec{\Delta}_j = \{\Delta_{xj}, \Delta_{yj}, \Delta_{zj}, \Delta_{gj}\} = \vec{\varsigma}_{Tj} - \vec{\varsigma}_{0j}$, and (eq. 12) --.

Column 14, line 19, " $\vec{\varsigma}_{Tj}\ \varsigma_{Tgj}$ " should read -- $\vec{\varsigma}_{Tj} \cdot \varsigma_{Tgj}$ --.

Column 14, line 59, "data were" should be --data was--.

Column 16, line 62, "target successful" should read --target was successful--.

Column 17, line 11, "multi jointed" should read --multi-jointed--.

Column 17, line 28, "other then" should read --other than--.

In the claims

Column 17, line 49, "parameters:" should read --parameters: and--.

Column 20, line 29, "an" should read --and--.